United States Patent
House et al.

(10) Patent No.: US 7,449,327 B2
(45) Date of Patent: Nov. 11, 2008

(54) SYSTEM AND METHOD FOR DISPENSING DEHYDRATED CULTURE MEDIA POWDER

(75) Inventors: Arthur G. House, Chevy Chase, MD (US); Kevin P. Klink, Middletown, MD (US); William J. Richman, Frederick, MD (US)

(73) Assignee: Mediatek, LLC, Frederick, MD (US)

( * ) Notice: Subject to any disclaimer, the term of this patent is extended or adjusted under 35 U.S.C. 154(b) by 244 days.

(21) Appl. No.: 11/119,792

(22) Filed: May 3, 2005

(65) Prior Publication Data

US 2006/0252145 A1    Nov. 9, 2006

(51) Int. Cl.
*C12M 1/00* (2006.01)
*C12N 1/00* (2006.01)

(52) U.S. Cl. .................... 435/283.1; 435/243

(58) Field of Classification Search .............. 435/243, 435/283

See application file for complete search history.

(56) References Cited

U.S. PATENT DOCUMENTS

| | | | |
|---|---|---|---|
| 3,406,870 A * | 10/1968 | Arneson | 222/57 |
| 3,501,379 A * | 3/1970 | Tate | 435/286.4 |
| 5,385,403 A | 1/1995 | Knight et al. | |
| 5,899,248 A * | 5/1999 | Anderson | 141/358 |
| 6,173,117 B1 * | 1/2001 | Clubb | 392/442 |
| 6,199,605 B1 | 3/2001 | Inaba et al. | |
| 2004/0026452 A1 | 2/2004 | Santiago et al. | |

FOREIGN PATENT DOCUMENTS

GB    2187373 A    9/1987

OTHER PUBLICATIONS

Serpent & Dove advertisement, "New: Magnetic Mount for Vibrating Motors," www.serpent-dove.com, May 13, 2005.
Kinematics Models 4400/VC and 4400/TX, www.kinematics.com/products/fillingMachines.html, 2005.

* cited by examiner

*Primary Examiner*—Jon Weber
*Assistant Examiner*—Kailash C Srivastava
(74) *Attorney, Agent, or Firm*—Drinker Biddle & Reath LLP

(57) ABSTRACT

An improved system and method for dispensing dehydrated culture media (DCM) powder into containers for preparation as a culture media. The manual and automated systems and methods operate to dispense DCM powder, as well as liquid, into vessels or media preparation instruments in a manner to avoid DCM dust inhalation by persons in the surrounding area and contamination of equipment and surfaces in the surrounding area.

17 Claims, 5 Drawing Sheets

SYSTEM AND METHOD FOR DISPENSING DEHYDRATED CULTURE MEDIA POWDER

BACKGROUND OF THE INVENTION

1. Field of the Invention

The present invention provides an improved system and method for dispensing dehydrated culture media (DCM) powder into containers for preparation of culture media. More particularly, the present invention relates to improved manual and automated systems and methods for dispensing DCM powder into vessels or media preparation instruments in a sanitary manner to avoid contamination by DCM powder dust to the surrounding area.

2. Description of the Related Art

Microbiology laboratories are required to produce large quantities of agar based growth media to use in the growth of bacteria and other microorganisms. Regardless of the specific agar media formulation used, most media are prepared by mixing powdered dehydrated culture media (DCM) with water and then sterilizing the mixture in an autoclave to insure the growth media is free of contamination. The dehydrated media powder, which is ground very fine, is typically delivered to the laboratory in plastic containers of varying sizes. A laboratory technician will typically scoop or pour out and weigh the required amount of DCM powder, add the appropriate amount of water, and mix and warm the mixture using, for example, a magnetic stirring motor with stir bar. Once the DCM and water have been completely mixed, the mixture is sterilized by autoclave or media preparator.

As used in most laboratories, DCM is a very light and fine powder. Some DCM formulations are highly toxic and all are irritants to some degree. When poured, DCM often forms a cloud of dust that rises above and around the technician who is dispensing the powder. This "media cloud" or "dusting" causes several problems. Often the technician will inhale DCM dust, which can be a health hazard. Additionally, as the dust settles it leaves a film of agar on surrounding laboratory surfaces. Because DCM typically is used in areas that tend to be warm and moist due to the close proximity of steam-producing autoclaves, the media dust leaves a sticky film that is difficult to clean and that increases the likelihood of surface contamination. Moreover, because the DCM is a fine powder, it tends to penetrate into very small spaces in the laboratory, including the inside surfaces of scientific instruments where the resulting film can cause damage and excess wear over time.

Another problem is that the process of dispensing DCM is time consuming since a precise quantity should first be weighed prior to adding water. A further problem is that mixing large batches of DCM with water, e.g., batches of certain types of media larger than 10 liters, often requires DCM and water to be added alternately in limited quantities each time to avoid clumping of the media. This increases the time needed to create the media, contributes to inaccuracies and errors and increases the likelihood of DCM dusting. A further problem is that technicians sometimes are imprecise in their measurements of DCM or water. It is also important for technicians to be able to readily identify different containers including different types of media cultures without close inspection, to thus increase the efficiency of the dispensing process.

Accordingly, a need exists for an improved system and method for dispensing DCM in a sanitary manner to avoid contamination to surrounding areas and minimize exposure to technicians and other personnel.

SUMMARY OF THE INVENTION

An embodiment of the present invention provides an automated or manual system for delivering DCM powder to a preparation instrument or a container in a sanitary manner to prevent media dusting by eliminating or substantially reducing the formation of the DCM media cloud during the preparation process. An embodiment of the present invention further provides a method for a convenient, rapid, exact and reproducible dispensing of DCM into either flasks or automated media sterilizers or other instruments.

The embodiments of the present invention further are capable of dispensing an appropriate amount of water or liquid into a media sterilizer or other instrument or container while simultaneously dispensing DCM powder in the proper amount and in a manner so as to avoid clumping. The metering device can be programmable to dispense the appropriate admixture of water and DCM depending on the concentration desired. The embodiments of the present invention are also able to prevent or minimize laboratory errors by applying color coding or other identification indicia to the DCM containers to indicate specific media formulations, thereby reducing the likelihood that the incorrect DCM formulation will be used by a technician.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
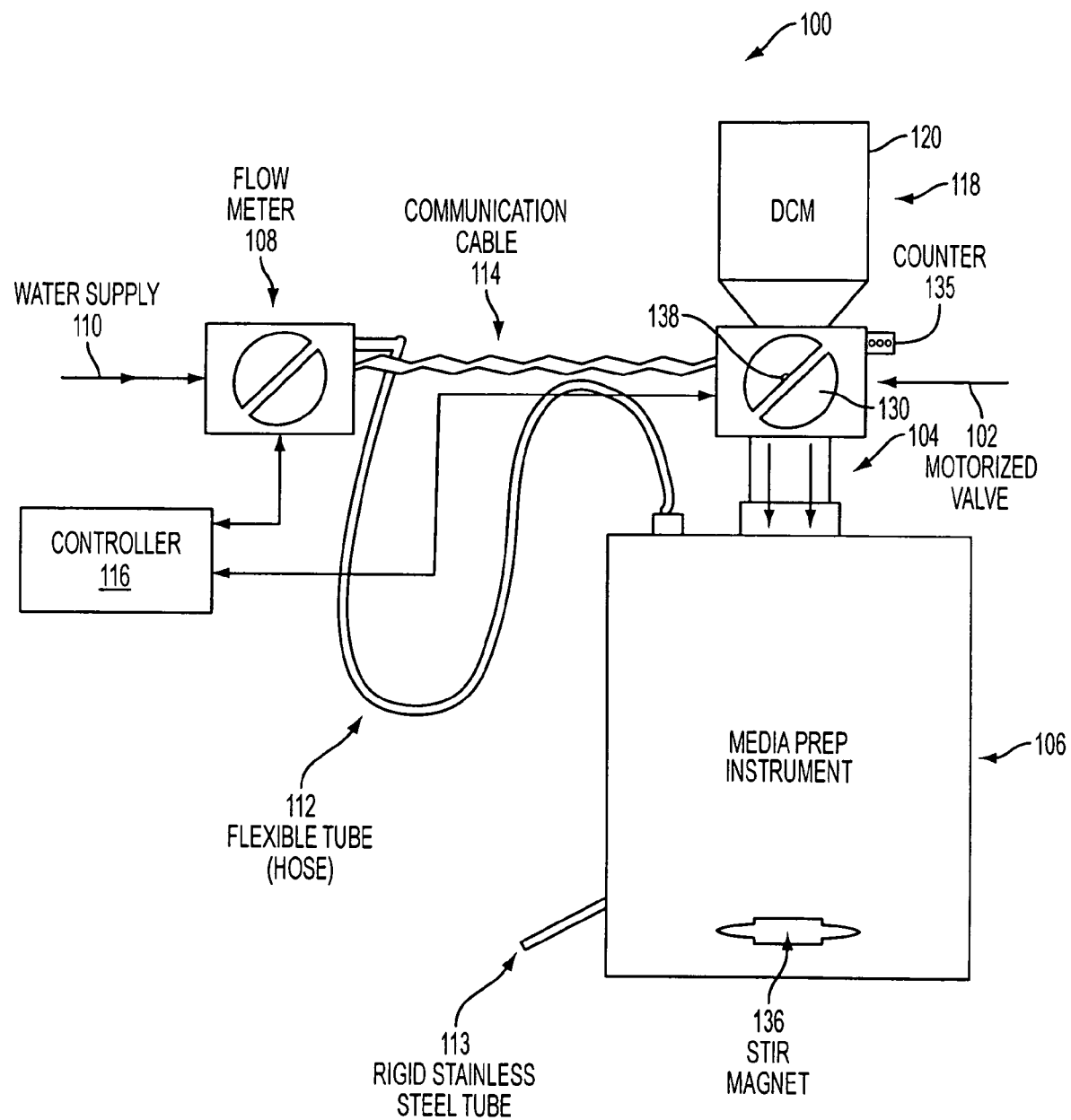
FIG. 1 is a conceptual block diagram illustrating an example of an automated system for dispensing DCM powder into a media preparation instrument according to an embodiment of the present invention.

FIG. 1 illustrates an automated system 100 for dispensing DCM powder according to an embodiment of the present invention. As illustrated, the automated system 100 includes a motorized valve assembly 102 that is connected via a conduit 104 to a media preparation instrument 106. The media preparation instrument can be any type of instrument such as the MediaPrep line from Systec Gmbh, Wettenberg, Germany, Masterclave line from AES Laboratoire, Rennes, France, or MediaClave line from Integra Biosciences, Chur, Switzerland, each of which are commercially available.

As further illustrated, the system further includes a flow meter 108. The flow meter is electronically controlled with a digital or analog input and output for communication with a secondary device used to inject the DCM powder into the system. The flow meter can work on the basis of peristaltic action or other common commercial methodologies such as magnetic, ultrasonic, positive displacement or differential pressure. The flow meter instrument can be any type of instrument such as the AES PM05 from AES Laoratoire, Rennes, France, or the Perimatic GP or Perimatic Premier from Jencons Scientific, Inc., Bridgeville, Pa., that is connected to a water supply 110 or other liquid supply and provides water or other liquid to the media preparation instrument 106 in a regulated manner via flexible tube 112 as discussed in more detail below. The tube 112 is connected to a rigid tube 113 made of, for example, stainless steel or any other suitable material, and which extends near the bottom of the interior of the media preparation instrument 106 to minimize clumping of the DCM powder 120 and to improve mixing. The rigid tube 113 allows water to be added below the surface line of the DCM mixture to prevent or decrease the incidence of splashing or bubbling to prevent or substantially prevent, or at least minimize, the contact of water with the media entry port. A flexible tube may be utilized in place of the rigid tube 113; provided such flexible tube is configured so as to prevent or decrease the incidence of splashing or bubbling in the media preparation device. In practice, the tube 113 can be of any suitable material, such as rigid plastic, flexible plastic, bendable metal, a flexible hose, and so on, as long as it is positioned to prevent or substantially prevent the incidence of splashing or bubbling and its opening is at a sufficient distance from the media entry port. The motorized valve assembly 102 and flow meter 108 are connected by a communication cable 114 so that the rate at which the DCM powder is dispensed by the motorized valve 102 is coordinated with the rate at which liquid is dispensed into the media preparation instrument 106 by the flow meter 108 under the control of a controller 116, which can be a processor or any type of computer as can be appreciated by one skilled in the art. The controller 116 can be programmable by the technician or other suitable personnel as desired and with ease to control the desired dispensing rate of the DCM powder and liquid as discussed in more detail below. As further illustrated, the motorized valve 102 receives a container 118 in which the DCM powder is stored.

Figure 2:
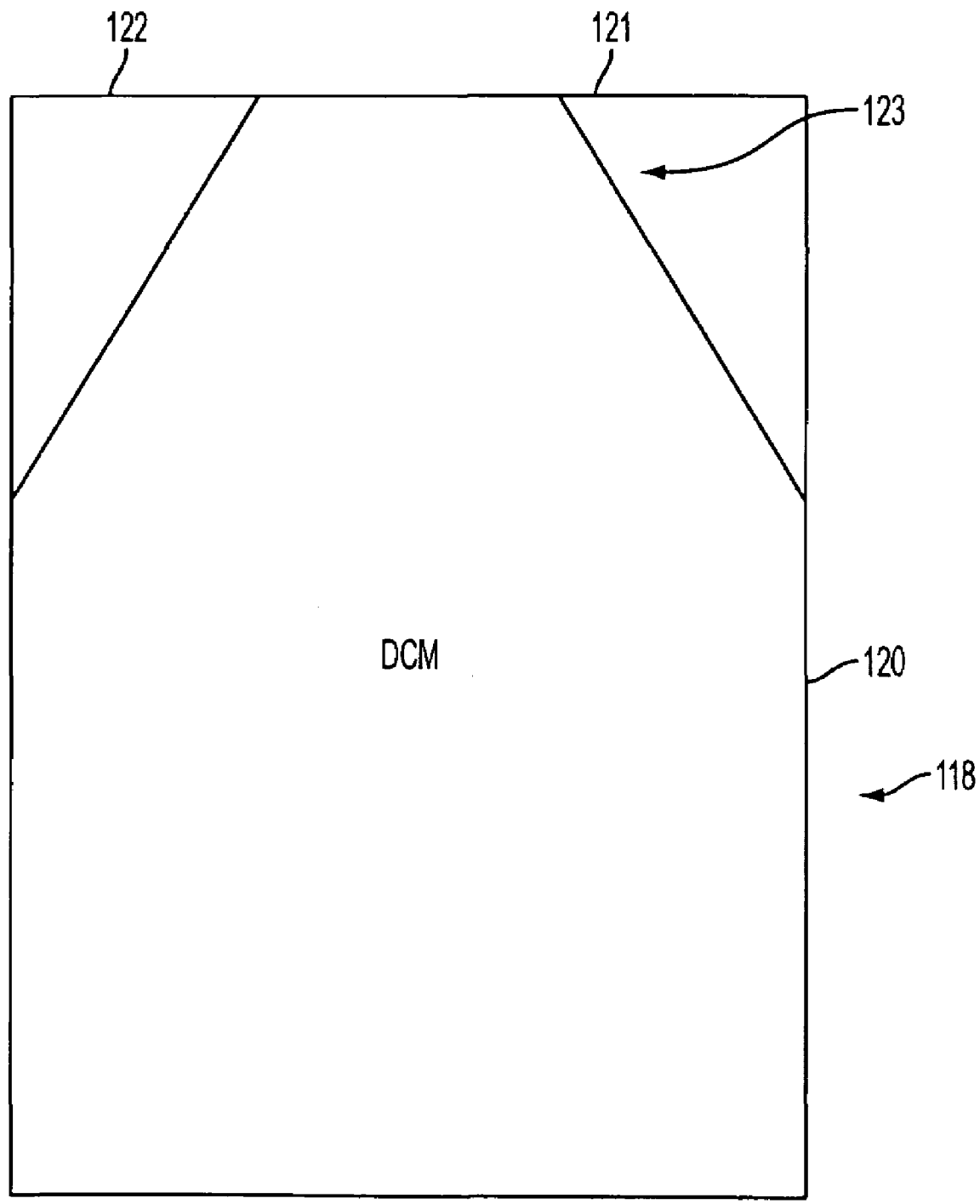
FIG. 2 is an example of a container which stores the DCM powder according to an embodiment of the present invention.
Figure 3:
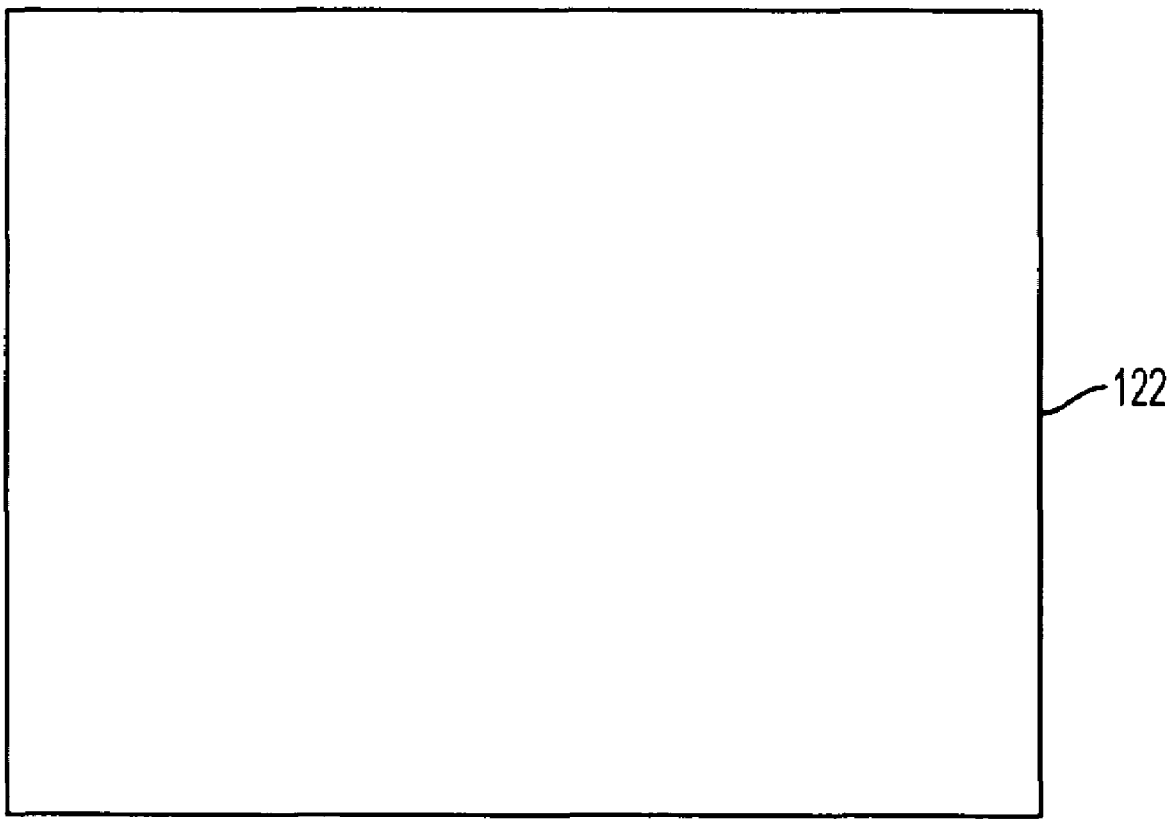
FIG. 3 is a top view of the container as shown in FIG. 2.

An example of a container for storing the DCM powder is shown in FIG. 2. In particular, the container 118 includes a container portion 120 and a cap 122. The container portion 120 can be any shape, although according to an embodiment of the present invention, it is advantageous for stacking purposes for the container to be shaped in the form of a rectangle or square having flat or substantially flat sides as shown in FIG. 2 and in the top view of FIG. 3. As further illustrated in FIG. 3, the cap 122 is preferably square shaped and has a flat or substantially flat top surface to allow the containers to be stacked vertically. The width and length of the cap 122 can correspond to the width and length of the container portion 120 as shown, or can be less than or greater than the width and length of the container portion 120, as deemed suitable for storage and stacking purposes.

In addition, for identification purposes, the container portion 120 and the cap 122 can be coded with a color or other indicator representing the contents of the container 118. For instance, this identification can be a color coding (e.g., red, green, blue, etc.) that is present on portions or the entirety of the container portion 120 and cap 122, a type of indicia (e.g., numbers, letters or alphanumeric symbols) on the container portion 120 and cap 122 representing the content of the container, and/or a bar code representing the content of the container 118. Various safety warnings and other relevant information can also be present on the container portion 120, cap 122 or both. Also, the container portion 120 and cap 122 can be made of any suitable material, such as plastic or various polymers, and can be opaque, or can be translucent so that a technician can readily determine the amount of DCM powder remaining in the container. Furthermore, the mouth of the container portion 120 is tapered or conical in shape so as to allow the DCM powder to readily flow from the container portion 120 when the container portion 120 is set in an upside down position with the cap 122 removed, and includes threads 121 as indicated. The mouth of the container portion 120 and the cap 122 can have threads 123 so that the cap 122 can be screwed onto exterior threads on the container portion 120. The container portion 120 can also be configured to include threads 121 on its interior wall near its opening. In this event, the container portion 120 can be screwed onto the motorized valve assembly 102 of FIG. 1 or the valve assembly 146 of FIG. 6, or directly onto the inlet of the media preparation instrument 106, regardless of whether the motorized valve assembly 102, valve assembly 146 or the inlet of the media preparation instrument 106, has interior or exterior threads. Alternatively, the cap 122 can be snap-fit onto the container portion 120, and the container portion 120 can simply be placed in an inverted manner so that its opening is received into the opening in the motorized valve assembly 102, valve assembly 146 or the inlet of the media preparation instrument 106.

Figure 4:
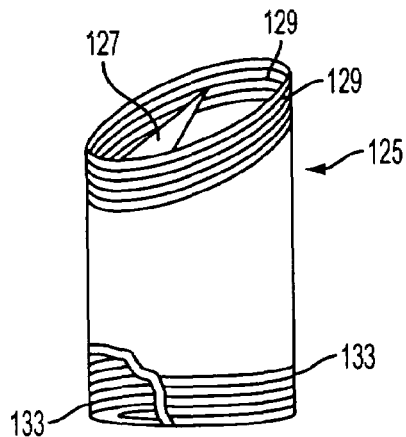
FIG. 4 illustrates an example of an adapter according to an embodiment of the present invention, that can be used with the container shown in FIG. 2.

In addition, it should be noted that the container portion 120 can have a volume that contains a pre-measured, pre-packaged quantity of DCM powder for a single-use, so that the container 118 can be discarded after its DCM powder contents has been dispensed as discussed in more detail below. It should be further noted that the container 118 can alternatively be configured as a burstable pouch or bag, for example, that contains a pre-measured, pre-packaged amount that can be dispensed directly into the media preparation instrument 106, into the media preparation instrument 106 via an adapter 125 as shown in FIG. 4, or into the motorized valve assembly 102 when pressure is applied to the container portion 120 to burst the container 120, and then the container portion 120 can be discarded. Concerning the adapter 125, as indicated in FIG. 4, the adapter 125 can be shaped at an angle, or can include a lancet 127, such that when the container portion 120 is mated with the adapter 125, the lancet 127 or angled portion of the adapter 125 pierces a membrane (e.g., a rupturable membrane) present at the mouth of the container portion 120. Furthermore, the adapter can have threads 129 that mate with the threads 123 on the outside of the container portion 120 so that the container portion 120 can be screwed onto the adapter 125. It is further noted that the threads 123 can also be present on the outside of the adapter 125 as indicated, to mate with interior threads of the container portion 120 should such an arrangement be necessary. The other end of the adapter 125 can include threads 133 that can be on the exterior surface of the adapter 125, the interior surface of the adapter 125 (as indicated by the breakaway section), or both, to allow the adapter 125 to mate with the motorized valve assembly 102, valve assembly 146 or the inlet of the media preparation instrument 106, regardless of whether the threads of the valves 102 or 146, or at the inlet of the media preparation instrument 106, are exterior or interior.

Figure 5:
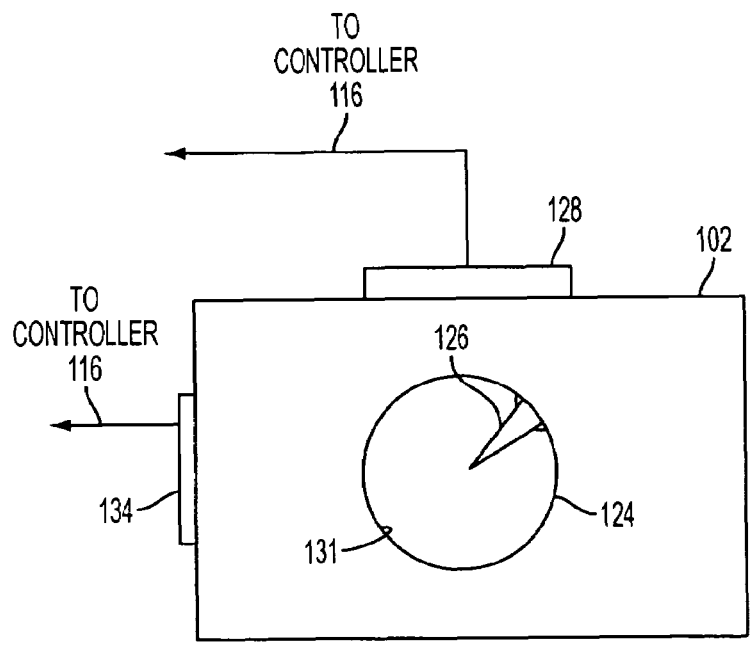
FIG. 5 is a detailed top view of the portion of the motorized valve assembly of the system shown in FIG. 1 that receives the mouth of the DCM container according to the embodiment of the present invention.

An example of the operation of the automated system 100 will now be described with reference to FIG. 1. As indicated, the cap 122 is removed from the container 118 and the container portion 120 is placed in an upside-down vertical or substantially vertical position on the top of the motorized valve assembly 102. As shown in FIG. 5, the mouth 124 of the motorized valve assembly 102 can have a lancet 126 or other suitable puncturing mechanism for puncturing any membrane (e.g., a rupturable membrane) that may be present at the mouth of the container portion 120, so that the DCM powder can be gravity-fed into the motorized valve assembly 102. The inner surface of the mouth 124 of the motorized valve assembly 102 can also include threads 131 that can mate with the threads 123 at the outside mouth of the container portion 120 as the container portion 120 is mated with the motorized valve assembly 102. Alternatively, the mouth of the container portion 120 can simply mate with the mouth 124 of the motorized valve assembly 102 in any suitable manner. As noted above, the adapter 125 can be used to couple the container portion 120 to the mouth 124 of the motorized valve assembly 102. In this regard, the adapter can have threads 133 that mate with the threads 131 on the inner surface of the mouth 124 of the motorized valve assembly 102. In any event, the mating of the container portion 120 and the mouth 124 of the motorized valve assembly 102, either directly or via the adapter 125, as well as the mating of the container portion 120 with the media preparation instrument 106 directly or via the adapter 125, form a closed or substantially closed system that eliminates or at least substantially eliminates DCM dust formation outside of the media preparation instrument 106. The mouth 124 of the motorized valve assembly 102 can alternatively be configured to mate with a container 118 that is configured as a burstable pouch or bag as discussed above, either directly or via the adapter 125 in any of the manners described above, so that when pressure is applied to the container portion 120, the pre-measured amount of DCM powder is dispensed into the motorized valve assembly 102 while maintaining the closed system to eliminate or at least substantially eliminate DCM dusting, and then the container portion 120 and cap 122 can be discarded.

Figure 6:
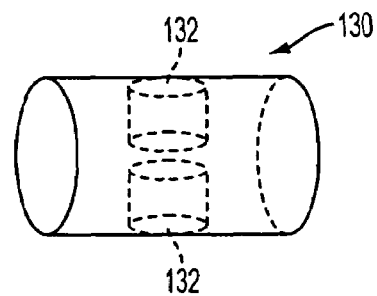
FIG. 6 illustrates an example of the features of the rotatable valve of the valve assembly shown in FIG. 1 for dispensing the DCM powder in a measured fashion according to an embodiment of the present invention.

As further illustrated in FIG. 5, the motorized valve assembly 102 can include a motor 128, such as a DC servo motor, a stepper motor, or any other suitable motor, that can be controlled by the controller 116 to rotate a rotatable valve 130 of the motorized valve assembly 102 that is shown in FIG. 1 and in more detail in FIG. 6. As indicated, the rotatable valve 130 includes wells 132 having a volume corresponding to a desired volume or mass of DCM powder (e.g., 15 grams) that is to be dispensed into the media preparation instrument 106. That is, the rotatable valve 130 is rotated at a desired rate as controlled by the controller 116 to periodically dispense the appropriate amount of DCM powder into the media preparation instrument 106 via the conduit 104. In addition, as the rotatable valve 130 is being rotated under the control of the controller 116, the flow meter 108 is controlled by the controller 116 to dispense an appropriate amount of liquid into the medium preparation assembly 106 via the tube 112. The ratio of dehydrated media to liquid is user controllable. For example, in a 100 liter preparation, one-fifth of the total DCM to be solubilized is added with every 20 liters of water. The user is able to define any ratio of total DCM to water, e.g., ¼ DCM combined incrementally with ¼ water or ⅓ DCM combined incrementally with ⅓ water. Accordingly, the rotatable valve 130 can be rotated more rapidly to dispense the DCM powder into the media preparation instrument 106 at a faster rate, while the controller 116 can proportionately control the flow meter 108 to increase the flow of liquid into the media preparation instrument 106. The motorized valve assembly 102 can further include a counter 135, such as a mechanical or digital counter as known in the art, that counts the number of rotations of the rotatable valve 130, and can be automatically or manually reset to zero after the desired amount of DCM powder has been dispensed.

It should be also noted that the rotatable valve 130 can be removed and replaced with another rotatable valve having wells of a different volume which thus feed a greater amount or lesser amount of DCM powder into the media preparation instrument 106 per each rotation. Furthermore, as shown in FIG. 5, the motorized valve assembly 102 can include an agitator 134, such as a vibrating coil or any other suitable component, to shake or vibrate the motorized valve assembly 102 to allow the DCM powder to more freely flow through the motorized valve assembly 102 and conduit 104 into the media preparation instrument 106.

It should also be noted that the rotatable valve 130 can include a handle 138 that can be turned manually if is desired to operate the rotatable valve 130 manually. The flow meter 108 can also be operated manually if desired. As further indicated, the media preparation instrument 106 includes a stirrer magnet 136 as known in the art which can provide further stirring and agitation of the powder and liquid mixture in the media preparation instrument 106. It can be further noted that the controller 116 can be connected by any suitable means to the controller (not shown) of the media preparation instrument 106 to increase or decrease the rate of stirring by the stirring magnet 138 depending on the rate of deposit of DCM powder and liquid by the motorized valve assembly 102 and flow meter 108. Accordingly, this system 100 allows for the accurate dispensing of DCM powder and liquid into the media preparation instrument 106 in a clean and sanitary manner, with little or no waste of the DCM powder, minimal contamination of the surrounding areas due to dusting, and minimal exposure to the lab technician and other personnel due to dusting.

Figure 7:
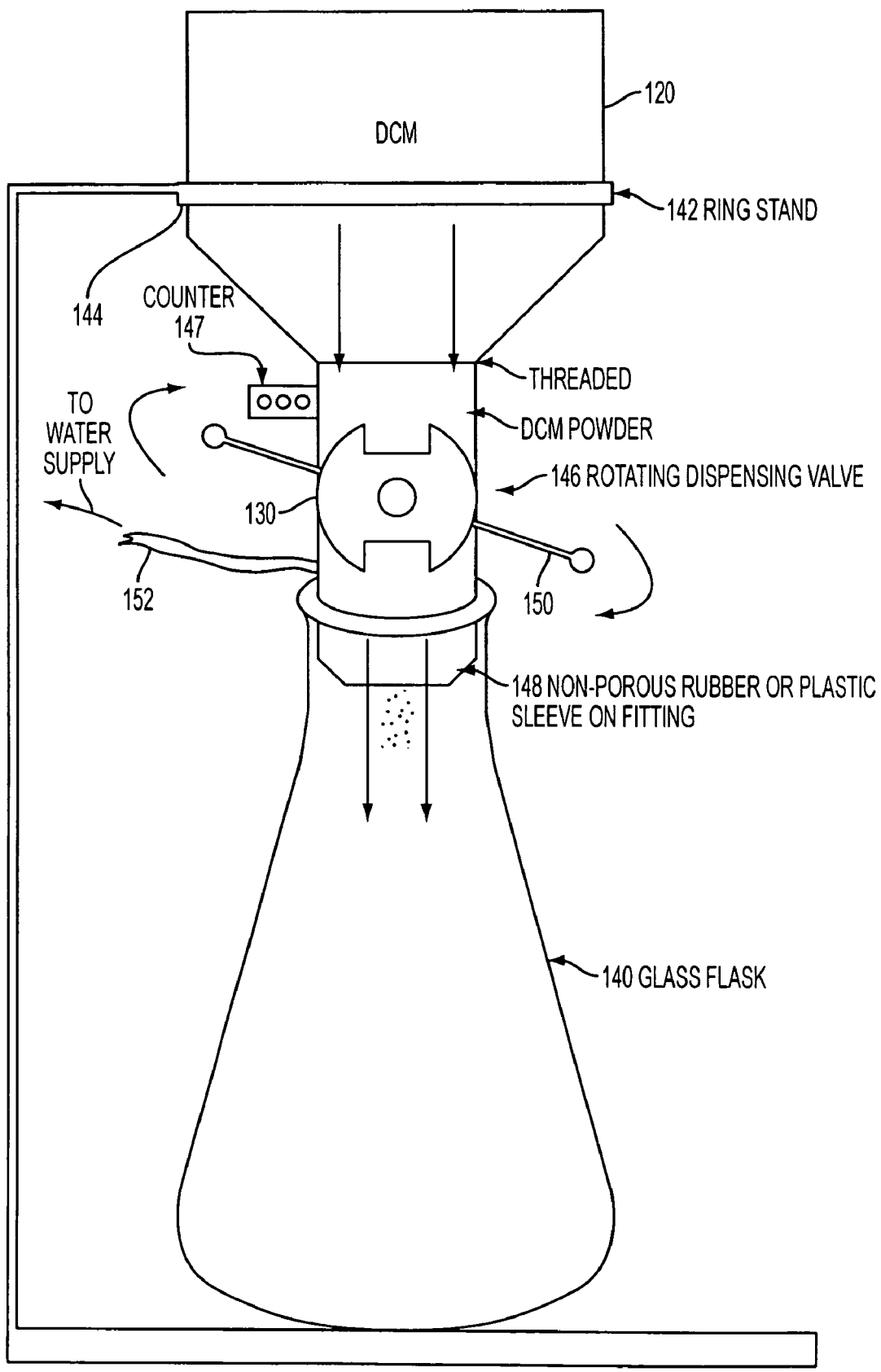
FIG. 7 illustrates an example of another system for dispensing DCM powder into a flask in a measured manner according to another embodiment of the present invention.

Although FIG. 1 and its related figures illustrate an automated system 100 for dispensing DCM powder into a media preparation instrument 106, the automated system 100, or a manual system, can be used to dispense the powder into another vessel or flask 140, such as an Erlenmeyer flask, as illustrated in FIG. 7. As indicated in FIG. 7, the system includes a ring stand 142 having a support 144 for supporting the container portion 120 in an upside down vertical or substantially vertical manner so that the DCM powder can flow by gravity into the valve assembly 146. The valve assembly 146 can include threads that mate with threads 123 on the outside of the mouth of the container portion 120, or the container portion 120 can simply be received into an opening in the valve assembly 146. Alternatively, the container portion 120 can be mated with the valve assembly 146 via the adapter 125 in the manner discussed above with regard to the motorized valve assembly 102, so as to form a closed or substantially closed system. Accordingly, the mating of the container portion 120 and the valve assembly 146, either directly or via the adapter 125, form a closed or substantially closed system that eliminates or at least substantially eliminates DCM dust formation outside of the vessel 140. The valve assembly 146 can alternatively be configured to mate, either directly or via the adapter 125, with a container 118 that is configured as a burstable pouch or bag as discussed above, so that when pressure is applied to the container 118, the pre-measured amount of DCM powder is dispensed into the valve assembly 146 when pressure is applied to the container 118 while maintaining the closed or substantially closed system to eliminate or at least substantially eliminate DCM dusting, and then the container 118 can be discarded. Furthermore, as can be appreciated from the above, the vessel 140 can be configured to mate with any of the types of container portion 120 directly or via the adapter 125 without using the valve assembly 146, and can have threads that mate with the threads 129 on the adapter 125 to facilitate the mating.

261 Also, the mouth of the valve assembly 146 can include a lancet similar to lancet 126 (see FIG. 5) to puncture any sealable membrane covering the mouth of the container portion 120. The valve assembly 146 further can be configured similar to the automated valve assembly 102, or can be configured solely as a manual valve assembly in which a user such as lab technician rotates the rotatable valve 130 of the valve assembly 146 by turning a knob 150 or by any other suitable mechanism. As with the motorized valve assembly 102, the rotatable valve 130 of the valve assembly 146 can be removed and replaced with a rotatable valve having different size wells to dispense a different amount of DCM powder into the flask 142 per each rotation. The valve assembly 146 can further include a counter 147, such as a mechanical or digital counter as known in the art, that counts the number of rotations of the rotatable valve 130, and can be automatically or manually reset to zero after the desired amount of DCM powder has been dispensed.

As further shown, the valve assembly 146 can include a non-porous rubber or plastic sleeve 148 to allow for mating with the mouth of the flask 142. Furthermore, the valve assembly 146 or the sleeve 148 can include an inlet tube 152 to allow water or other liquid to be manually or automatically fed into the flask 142 as the rotatable valve 148 is being manually or automatically rotated. The valve assembly 146 and the system in general can be automatically or manually agitated to allow the DCM powder to more freely fall into the valve assembly 146, and thus more freely into the flask 142. Accordingly, the system shown in FIG. 7 also provides an efficient and sanitary system for dispensing DCM powder into a container while avoiding waste and contamination of the surrounding area due to dusting and exposure to DCM powder inhalation due to dusting.

While this invention has been particularly shown and described with reference to preferred embodiments thereof, the preferred embodiments described above are merely illustrative and are not intended to limit the scope of the invention. It will be understood by those skilled in the art that various changes in form and details may be made therein without departing from the spirit and scope of the invention as defined by the appended claims.

What is claimed is:

1. A system for dispensing dehydrated culture media (DCM) powder from a container into a vessel, the system comprising:
    a valve assembly, being independent of the container and the vessel, and comprising:
        a structure defining a first opening therein and a second opening therein and an interior thereof, the first and second openings being on different sides of the structure, with the first opening being configured to couple the interior of the structure into communication with an opening that has been created in a container to provide communication between the interior of the structure and an interior of the container that houses DCM powder, and the second opening being configured to couple the interior of the structure into communication with an inlet that has been created in the vessel to provide communication between the interior of the structure and an interior of the vessel, such that the coupling together of the structure, container and vessel creates a substantially closed system to substantially eliminate DCM dust formation outside of the vessel; and
    a valve, disposed in the interior of the structure, and operable to dispense the DCM powder from the container such that the DCM powder enters the interior of the structure through the first opening, is driven by the movable valve through the interior of the structure, and passes out of the second opening at a rate controlled by movement of the movable valve and through the inlet into the vessel while the substantially closed system substantially eliminates DCM dust formation outside the vessel, structure and container; and
    a liquid regulator, adapted to control a flow of liquid into the vessel.

2. A system for dispensing dehydrated culture media (DCM) powder into a vessel which is a media preparation instrument, the system comprising:
    a valve, having an opening and adapted to couple to a container including DCM powder, and adapted to operate to dispense the DCM powder from the container at a rate into the vessel; and
    a conduit, adapted to add liquid to the media preparation instrument at a sufficient distance from an inlet of the media preparation instrument into which the valve dispenses the DCM powder to substantially prevent the contact of the liquid with the DCM powder at the inlet.

3. A system as claimed in claim 1, further comprising:
    a controller, adapted to automatically control the valve to dispense the DCM powder into the vessel at the rate.

4. A system as claimed in claim 1, further comprising:
    a handle, adapted to enable a user to manually operate the valve to dispense the DCM powder into the vessel at the rate.

5. A system as claimed in claim 1, further comprising: a controller, adapted to automatically control the valve to dispense the DCM powder into the vessel at the rate while also controlling the liquid regulator to control the flow of liquid into the vessel at a flow rate.

6. A system as claimed in claim 1, wherein: at least one of the valve and the liquid regulator is manually operable to control at least one of the rate at which the DCM powder is dispensed into the vessel and a rate of flow of the liquid into the vessel.

7. A system as claimed in claim 1, wherein: the vessel is a flask.

8. A system as claimed in claim 1, wherein: the vessel is a media preparation instrument.

9. A system as claimed in claim 1, further comprising:
    an adapter, configured to couple between the first opening in the structure and the opening in the container to couple the container to the valve assembly while maintaining the substantially closed system.

10. A system as claimed in claim 1, wherein: the valve further comprises a rotatable member that is adapted to rotate and dispense an amount of the DCM powder into the vessel per each rotation.

11. A system as claimed in claim 1, wherein:
    the valve is rotatable about an axis which is transverse to a direction of flow of the DCM powder through the structure.

12. A system as claimed in claim 8, further comprising: a conduit adapted to add liquid to the media preparation instrument at a sufficient distance from an inlet of the media preparation instrument into which the valve dispenses the DCM powder to substantially prevent the contact of the liquid with the DCM powder at the inlet.

13. A system as claimed in claim 10, wherein: the valve further comprises a counter that is adapted to count the number of rotations of the rotatable member.

14. A system as claimed in claim 11, wherein:

the valve has at least one recess therein for receiving an amount of DCM powder therein, such that a volume of the recess governs the rate at which the valve dispenses the DCM powder when the valve rotates at a rotational rate about the axis.

15. A system as claimed in claim 14, wherein:

the valve has a plurality of recesses therein disposed at a distance from each other about an exterior surface of the valve, such that when the valve rotates to position Me of the recesses containing DCM powder at an orientation facing the second opening of the structure, the DCM powder falls out of said one of the recesses and out of the second opening of the structure.

16. A system as claimed in claim 15, wherein:

the valve controls the rate at which the DCM powder is dispensed by controlling a rate at which the plurality of recesses are positioned at the orientation facing the second opening of the structure.

17. A system as claimed in claim 16, wherein:

the valve is removable from the structure and replaceable with a second valve having at least one recess therein whose volume is different from the volume of the recess in the valve, to enable the second valve to dispense the DCM powder at a second rate different from the rate at which the valve dispenses the DCM powder when the second valve is rotated at the rotational rate.

* * * * *